US008653266B2

(12) United States Patent
Gore et al.

(10) Patent No.: US 8,653,266 B2
(45) Date of Patent: Feb. 18, 2014

(54) PROCESS FOR THE PRODUCTION OF ETRAVIRINE

(75) Inventors: Vinayak Gore, Hyderabad (IN); Choudhari Bharati, Hyderabad (IN); Mahesh Hublikar, Hyderabad (IN); Prakash Bansode, Hyderabad (IN); Sandip Sinore, Hyderabad (IN)

(73) Assignee: Mylan Laboratories Limited, Hyderabad (IN)

( * ) Notice: Subject to any disclaimer, the term of this patent is extended or adjusted under 35 U.S.C. 154(b) by 0 days.

(21) Appl. No.: 13/456,319

(22) Filed: Apr. 26, 2012

(65) Prior Publication Data

US 2013/0116433 A1    May 9, 2013

(30) Foreign Application Priority Data

Apr. 26, 2011 (IN) .......................... 1441/CHE/2011

(51) Int. Cl.
*C07D 239/24* (2006.01)

(52) U.S. Cl.
USPC ............................ 544/316; 544/242; 544/298

(58) Field of Classification Search
USPC .................................. 544/242, 298, 315, 316
See application file for complete search history.

(56) References Cited

U.S. PATENT DOCUMENTS

| 8,153,790 B2 * | 4/2012 | Krizmani et al. ............. 544/317 |
| 8,173,623 B2 * | 5/2012 | Crawford et al. ............. 514/100 |

* cited by examiner

*Primary Examiner* — Golam M Shameem
(74) *Attorney, Agent, or Firm* — Ladas & Parry LLP

(57) ABSTRACT

A novel process for the preparation of Etravirine comprises the condensing of ethyl cyanoacetate with N-cyanophenylguanidine to obtain an —OH compound of formula (II), which is further converted to a leaving group of formula (III). The compound of formula (III) is optionally protected and brominated to yield compound of formula (IV). The condensation of formula (IV) with 3,5-dimethyl-4-hydroxybenzonitrile yields a compound of formula (VI), and an optional deprotection of the compound of formula (VI) results in Etravirine.

11 Claims, No Drawings

PROCESS FOR THE PRODUCTION OF ETRAVIRINE

The present application claims the benefit of Indian application 1441/CHE/2011 filed Apr. 26, 2011, the contents of which are incorporated herein by reference.

FIELD OF THE INVENTION

The present invention relates to novel method for synthesis of the non-nucleoside reverse transcriptase inhibitor 4-[[6-amino-5-bromo-2-[(4-cyanophenyl)amino]-4-pyrimidinyl]oxy]-3,5 dimethylbenzonitrile (Etravirine).

BACKGROUND OF THE INVENTION

4-[[6-amino-5-bromo-2-[(4-cyanophenyl)amino]-4-pyrimidinyl]oxy]-3,5 dimethylbenzonitrile, Etravirine (I), is marketed under the brand name of INTELENCE by Tibotec.

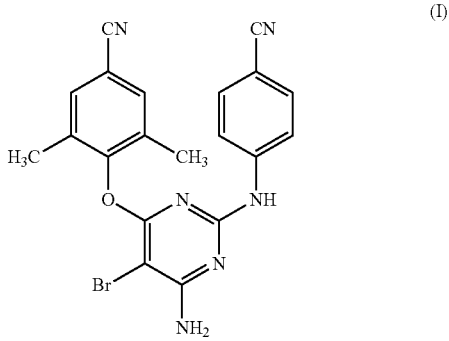 [SMILES: Cc1cc(C#N)cc(C)c1Oc1nc(Nc2ccc(C#N)cc2)nc(N)c1Br]

(I)

INTELENCE is a non-nucleoside reverse transcriptase inhibitor (NNRTI) of human immunodeficiency virus type 1 (HIV-1). Reverse transcriptase is a viral DNA polymerase enzyme that HIV needs to reproduce. Intelence blocks the enzymatic function of reverse transcriptase and prevents completion of synthesis of the double-stranded viral DNA, thus preventing HIV from multiplying.

Etravirine and its production method were first reported in U.S. Pat. No. 7,037,917. This method of synthesizing Etravirine describes treating 4-[[5-bromo-4-(4-cyano-2,6-dimethylphenoxy)-6-chloro-2-pyrimidinyl]amino]benzonitrile with $NH_3$ in the presence of 1,4-dioxane in a pressure vessel at 150° C. for 4 days.

Drugs of the Future 2005, 30(5): 462-468 discloses that 4-guanidinobenzonitrile is cyclized with diethylmalonate by means of sodium ethoxide to give 4-(4,6-dihydroxypyrimidine-2-yl-amino)-benzonitrile, which upon treatment with $POCl_3$ yields the corresponding dichloro derivative. Further bromination with bromine and sodium bicarbonate in aqueous methanol affords 4-(5-bromo-4,6-dichloropyrimidin-2-ylamine)-benzonitrile, which on condensation with the sodium salt of cyano-2,6-dimethylphenolate in presence of N-methylpyrrolidone and dioxane gives 4-[[5-bromo-4-(4-cyano-2,6-dimethylphenoxy)-6-chloro-2-pyrimidinyl]amino]benzonitrile, followed by the aminolysis of the same intermediate yields Etravirine. It also discloses another process in which 5-bromo-2,4,6-trichloropyrimidine is reacted with 4-aminobenzonitrile in presence of diisopropylethylamine to give 4-(5-Bromo-4,6-dichloro-pyrimidin-2-ylamino)-benzonitrile, which is then reacted with 4-hydroxy-3,5-dimethylbenzonitrile to give 4-[[5-bromo-4-(4-cyano-2,6-dimethylphenoxy)-6-chloro-2-pyrimidinyl]amino]benzonitrile. The aminolysis of the same intermediate yields Etravirine.

WO 2010150279 describes a process for the formation of Etravirine, comprising condensation of 2,4,6-trichloropyrimidine with 3,5-dimethyl-4-hydroxybenzonitrile to give 4-[(2,6-dichloro)-4-pyrimidinyloxy]-3,5-dimethyl benzonitrile, which is condensed with 4-aminobenzonitrile. Aminolysis of the resulting compound followed by halogenation gives Etravirine.

The prior art processes for preparing Etravirine involve aminolysis. The reaction of a desired intermediate with ammonia even in refluxing dioxane requires more time for reaction completion. Therefore, there exists a need in the art for an improved process for the preparation of Etravirine, which is safe and commercially viable.

The present invention relates to a novel process for the preparation of Etravirine, which is commercially viable, less time cycle comparatively with prior art processes and it also provides novel intermediates which are useful in the preparation of Etravirine.

OBJECT OF THE INVENTION

The principle object of the present invention is to provide a novel method for the synthesis of Etravirine.

A further object of the present invention is to provide novel intermediates which are useful for the preparation of Etravirine.

Another object of the present invention is to provide Etravirine in high yield and high purity.

SUMMARY OF THE INVENTION

In one aspect, present invention provides a novel process for the preparation of Etravirine, comprising the steps of:
 a) condensing ethyl cyanoacetate with N-cyanophenylguanidine,
 b) converting OH— group of formula (II) into a leaving group of formula (III),
 c) optionally protecting the amino group of formula (III),
 d) brominating the compound of formula (IV),
 e) condensing the compound of formula (V) with 3,5-dimethyl-4-hydroxybenzonitrile, and
 f) optionally deprotecting the compound of formula (VI) to isolate Etravirine.

In another aspect, the present invention provides novel intermediates of formulas (II), (III), (IV), (V) and (VI).

In one more aspect, the present invention provides a process for purifying Etravirine comprising:
 a) dissolving Etravirine in a suitable solvent,
 b) removing the solvent,
 c) optionally adding water, and
 d) isolating pure Etravirine.

In another aspect, the present invention provides Etravirine in high yield and high purity.

DETAILED DESCRIPTION OF THE INVENTION

The present invention relates to a novel process for the preparation of Etravirine, and comprises condensing ethyl cyanoacetate with N-cyanophenylguanidine to obtain an —OH compound of formula (II), which is further converted to a leaving group of formula (III). The compound of formula (III) is optionally protected and brominated to yield the compound of formula (IV). Condensation of the compound of formula (IV) with 3,5-dimethyl-4-hydroxybenzonitrile gives the compound of formula (VI), and an optional deprotection of the compound of formula (VI) results in Etravirine.

The present invention further relates to a process for purifying Etravirine. The present invention also provides novel intermediates of Etravirine.

The main aspect of the present invention is to provide a novel method for the synthesis of Etravirine as shown in scheme I, comprising the steps of:

a) condensing ethyl cyanoacetate with N-cyanophenylguanidine, b) converting the OH— group of the formula (II) into a leaving group of formula (III), c) optionally protecting the amino group of the compound of formula (III) to yield the compound of formula (IV), d) brominating the compound of formula (IV) to yield the compound of formula (V), e) condensing the compound of formula (V) with 3,5-dimethyl-4-hydroxybenzonitrile to yield the compound of formula (VI), and f) optionally deprotecting the compound of formula (VI) to isolate Etravirine.

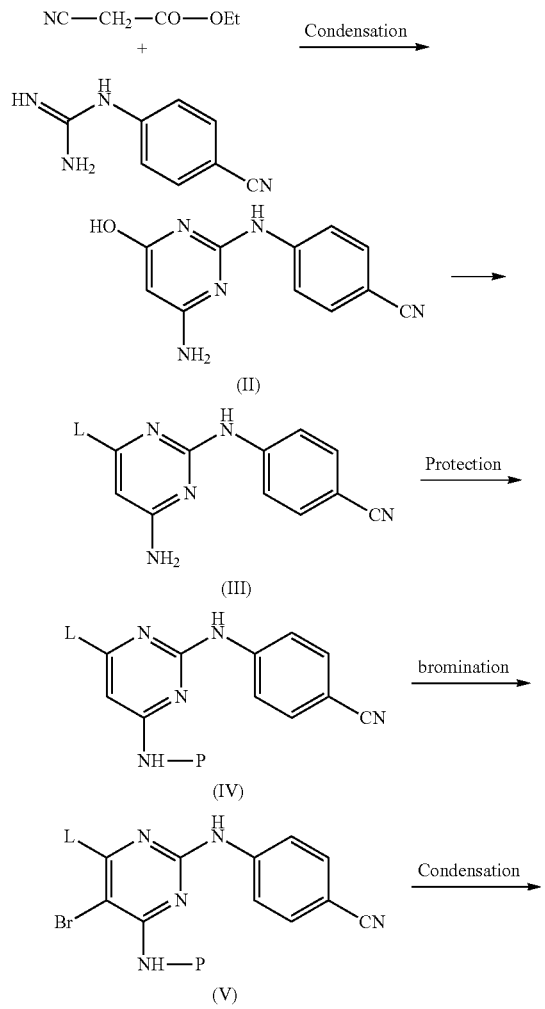

Scheme-1

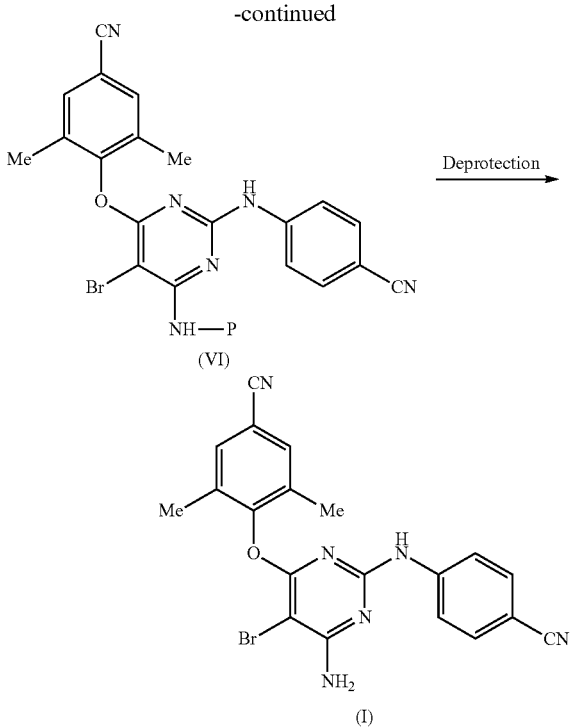

In one embodiment of the present invention, ethylcyano acetate is condensed with N-cyanophenyl guanidine to give 4-(4-amino-6-hydroxy-pyrimidin-2-ylamino)-benzonitrile of formula (II) in presence of a base in an organic solvent, wherein the base is selected from inorganic bases or organic bases. The inorganic base is selected from alkali metal alkoxides such as potassium-tert-butoxide, sodium-tert-buoxide, lithium-tert-butoxide preferably potassium tert butoxide; alkaline metal hydroxides such as sodium hydroxide, potassium hydroxide; alkaline metal carbonates such as sodium carbonate, potassiumcarbonate; and metal hydrides such sodium hydride. The organic bases are such as diethyl amine, triethyl amine, and pyridine. The organic solvent is selected from polar protic solvents such as methanol, ethanol, n-propanol, isopropanol, acetic acid, n-butanol, formic acid, and preferably n-butanol.

In another embodiment of the present invention, the —OH group of compound formula (II) is converted to yield the compound of formula (III), wherein L is a suitable leaving group, selected from a suitable leaving group known in the art, preferably chloro, bromo, tosylates, mesylates, and more preferably chloro. The conversion of the OH— group into the leaving group can be carried out by processes known in the art. The conversion of the OH— into the leaving group of the present invention, and preferably chloro, is carried out by treating the compound of formula (II) with a chlorinating agent selected from phosphorus oxychloride, phosphorus pentachloride, phosphorus trichloride, or thionyl chloride, and preferably phosphorus oxychloride.

In another embodiment of the present invention, the amine group of compound formula (III) is optionally protected with a suitable protecting group by treating with a suitable amino protecting agent in the presence of a base and solvent to give the compound of formula (IV), wherein the P is a protecting group selected from the amine protecting group such as carbobenzyloxy (Cbz), p-methoxybenzyl carbonyl, tert-butyloxycarbonyl (BOC), 9-fluorenylmethyloxycarbonyl (FMOC), acetyl (Ac), benzoyl (Bz), benzyl (Bn), carbamate group, p-methoxybenzyl (PMB), 3,4-dimethoxybenzyl (DMPM), p-methoxyphenyl (PMP), tosyl (Ts), other sulfonamides (Nosyl & Nps); and preferably a bezoyl group. The protection is carried out by treating the compound of formula (III) with bezoyl chloride in the presence of a base selected from triethylamine, diisopropylethylamine, 1,8-diazabicyclo[5.4.0]undec-7-ene (DBU), 1,5-diazabicyclo[4.3.0]non-5-ene (DBN), 1,4-diazabicyclo[2.2.2]-octane (DABCO), pyridine or 4-(dimethylamino)pyridine (DMAP), and preferably DMAP, and the solvent is selected from polar aprotic solvents such as acetone, tetrahydrofuran, methyl ethyl ketone, ethyl acetate, acetonitrile, N,N-dimethylformamide, and dimethyl sulfoxide; preferably acetonitrile. The protection can be carried out by following the procedure as described in Theodora W. Greene and Peter G. M. Wuts, *Protecting Groups In Organic Synthesis*, third edition, John Wiley and Sons, New York. N.Y.

In another embodiment of the present invention, 4-(4-optionally amino protected-6-leaving group substituted-pyrimidin-2-ylamino)-benzonitrile of formula (IV) is brominated with a brominating agent to give the compound of formula (V), wherein the bromination is carried out by treating with a brominating agent such as bromine in the presence of an acid such as acetic acid or N-bromosuccinamide, in a suitable organic solvent selected from inert solvents such as diethylether, chloroform, dichlromethane, and carbon tetrachloride; and preferably dichloromethane.

In another embodiment of the present invention, the brominated compound of formula (V) is condensed with 3,5-dimethyl-4-hydroxybenzonitrile to give the compound of formula (VI) in the presence of a base in a suitable solvent. The base is selected from triethylamine, diisopropylethylamine, 1,8-diazabicyclo[5.4.0]undec-7-ene (DBU), 1,5-diazabicyclo[4.3.0]non-5-ene (DBN), 1,4-diazabicyclo[2.2.2]-octane (DABCO), pyridine or 4-(dimethylamino)pyridine (DMAP), or combinations thereof; most preferably the combination of DBU and DMAP; The organic solvent is selected from polar aprotic solvents such as 1,4-dioxane, tetrahydrofuran, acetone, acetonitrile, N,N-dimethylformamide, and dimethyl sulfoxide; and preferably N,N-dimethylformamide.

Yet another embodiment of the present invention, the condensed compound of formula (VI) is optionally deprotected by treating with a base in a suitable solvent or mixtures thereof, wherein the base is selected from the alkali metal hydroxides such as sodium hydroxide, potassium hydroxide, and preferably lithium hydroxide; and an organic solvent or mixtures thereof selected from polar aprotic solvents and polar solvents such as methanol, ethanol, n-propanol, isopropanol, acetic acid, n-butanol, formic acid, acetone, tetrahydrofuran, methyl ethyl ketone, ethyl acetate, acetonitrile, N,N-dimethylformamide, and dimethyl sulfoxide; and preferably a mixture of acetonitirile and IPA.

In another aspect the present invention provides a process for purifying Etravirine comprising the steps of:

a) dissolving Etravirine in a suitable solvent;

b) removing the solvent;

c) optionally adding water; and d) isolating pure Etravirine.

In one embodiment of the present invention, the Etravirine is dissolved in a suitable solvent, wherein the suitable solvent is selected from water miscible solvents. A water miscible organic solvent is selected from polar solvents such as methanol, ethanol, isopropanol, n-propanol, acetone, acetonitrile, acetic acid and dioxane, and preferably acetone.

In another embodiment of the present invention, the solvent is removed from the Etravirine solution to obtain Etravirine solid. Preferably 60-90% and more preferable 70-80% of the solvent is removed from the Etravirine solution.

In one more embodiment of the present invention, to the obtained Etravirine solid is optionally added water and pure Etravirine is isolated.

According to the present invention, the crude Etravirine is purified by treating with a water miscible organic solvent, wherein the water miscible organic solvent is selected from polar solvents such as methanol, ethanol, isopropanol, n-propanol, acetone, acetonitrile, acetic acid, dioxane, and tetrahydrofuran, and preferably acetone. From the resulting solution around 70-80% of solvent is distilled off. The obtained solid is optionally treated with water to yield pure Etravirine.

Another aspect of the present invention is to provide novel intermediates of formula (II), (III), (IV), (V) and (VI) which are useful in the preparation of Etravirine,

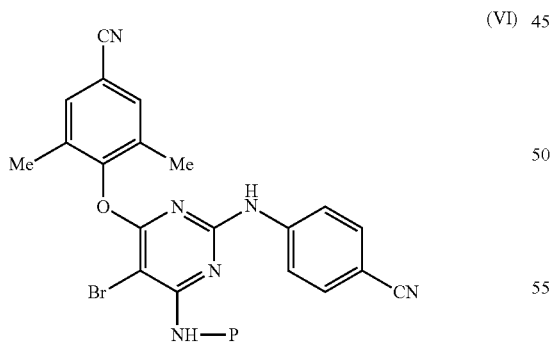
(VI)

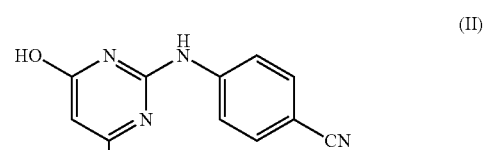
(II)

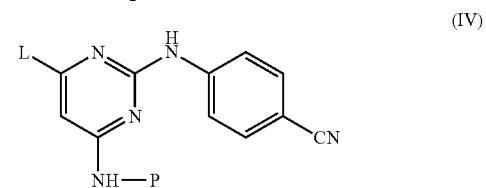
(IV)

L is leaving group, P is Hydrogen or protecting group.

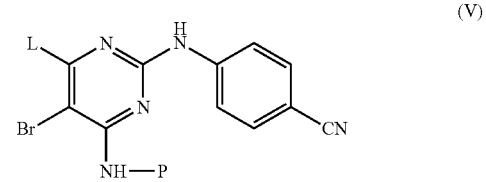
(V)

-continued

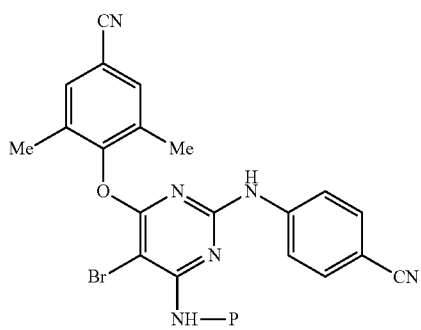

(VI)

wherein, L is a suitable leaving group and P is hydrogen or a suitable amino protecting group.

Certain specific aspects and embodiments are further explained in more detailed with the following examples. These examples should not be construed as limiting the scope of the invention in any manner.

EXAMPLES

Example 1

Preparation of 4-(4-amino-6-hydroxypyrimidin-2-ylamino)benzonitrile (II)

2000 ml of n-butanol and 192.8 g of potassium-tert-butoxide were added to the reaction vessel at 45±5° C. and stirred for 30 mins. To the reaction mixture was added 194.42 g of ethylcyano acetate over 15 min and added 250 ml of n-butanol. The reaction mixture was heated to 60±5° C. under stirring and 250 g of N-cyanophenyl guanidine was added, followed by 250 ml of n-butanol and further heated to 93±3° C., maintained the same at 4 hrs with stirring. After completion of the reaction, the reaction mixture was cooled to 75±5° C. and 1750 ml of water was added and stirred at the same temperature for 30 mins. Further to the reaction mass was added 250 ml of glacial acetic acid; stirred and cooled to room temperature (RT). The resulting solid was filtered and washed with 500 ml of water, followed by washing with methanol and drying to yield the titled compound.

Dry weight: 290-330 gm.

Example 2

Preparation of 4-(4-Amino-6-chloropyrimidin-2-ylamino)benzonitrile (III)

1900 ml of phosphorus oxychloride was added to a reaction vessel, to this was added 190 g of 4-(4-amino-6-hydroxypyrimidin-2-ylamino)benzonitrile under stirring at RT. The reaction mass was slowly heated to 80-85° C. and maintained at the same temperature for 16-18 hr. After completion of the reaction, phosphorous oxychloride was distilled off and stripped with 950 ml of ethyl acetate. 1900 ml of chilled water was slowly added to the reaction mass and its pH was adjusted to 9-10 with 950 ml of 50% aqueous potassium carbonate. The solid was filtered and dried under vacuum at 55-60° C. overnight.

Example 3

Preparation of 4-(4-amino-6-chloropyrimidin-2-ylamino)benzonitrile (III)

1500 ml of phosphorus oxychloride and 300 g of 4-(4-Amino-6-hydroxypyrimidin-2-ylamino)benzonitrile at 27±3° C. were added to the reaction vessel and heated to 97±3° C.; and maintained at same temperature for 7 hrs. After completion of the reaction, ~50% of phosphorous oxychloride was distilled off under vacuum at 83±2° C. and the reaction mixture was cooled to 30±5° C. In a clean RB flask were added 1000 g of ice and 1000 mL of water and such was slowly added the above obtained reaction mass. The pH of the reaction mass was adjusted to 9.0±0.5 with 50% potassium carbonate solution in water at 5±5° C. The reaction mixture was stirred, filtered and the obtained solid was washed with 600 ml of water and suck dried. The wet solid was charged into a RB flask at 27±3° C. to which was added 600 ml of water. The resulting wet solid was taken into a RB flask and 600 ml of water was added, stirred, and filtered. The obtained solid was washed with water and suck dried. 3000 ml of ethyl acetate was charged into a RB flask and to this was added the obtained solid and heated to 43±3° C. The reaction mass was stirred for 20 mins and filtered hot. The residue was washed with ethyl acetate and filtrate (1) collected at 27±3° C. The obtained solid was again taken in RB flask to which was added 1500 ml of ethyl acetate and heated to 43±3° C., stirred and the hot reaction mass filtered and the filtrate (2) collected. Both filtrates (1) and (2) were taken and distilled off solvent at 47±3° C. To the residue was added 900 ml of heptane and cooled to 27±3° C. and was again added 1100 ml of heptane, stirred, the solid filtered and suck dried, and the solid was washed with heptane. The obtained solid was dried under vacuum. To the obtained 190 g of crude was added 380 ml of dimethyl formamide and 20.4 ml of 1,8-diazabicycloundec-7-ene under stirring at 27±3° C. and the reaction mass heated to 47±3° C. To the obtained clear solution was added 760 ml of water and stirred for 1 hr. The reaction mass was cooled and filtered. The solid was washed with 760 mL of water twice and suck dried. The solid was washed with 48 ml of chilled methanol and the solid suck dried. The obtained solid was further dried under vacuum to yield the title compound.

Dry weight: 150-180 gm.

Example 4

Preparation of N-[6-chloro-2-(4-cyanophenylamino)pyrimidin-4-yl]benzamide (IV)

1400 ml of N-methylpyrrolidine and 140 g of 4-(4-Amino-6-chloropyrimidin-2-ylamino)benzonitrile was charged into a reaction vessel. To this were added 85.49 g of dimethylamino pyridine and 87.21 g of diazabicyclo undecene and stirred for 30 mins. To the reaction mixture was added 27.36 g of benzoyl chloride and stirred at RT for 30 mins. and heated to 80-85° C. and maintained the same for 4 hrs. After completion of the reaction, the reaction mass was cooled to RT and 1400 ml of water was added, followed by 1400 ml of 50% carbonate solution. The reaction mass was extracted with 1400 ml of dichloromethane and the dichloromethane layer was washed with 700 ml of water. The organic layers were separated and dried over anhydrous sodium sulfate and filtered; distilled off dichloromethane and the solid was isolated.

Example 5

Preparation of N-[6-chloro-2-(4-cyanophenylamino)pyrimidin-4-yl]benzamide (IV)

3000 ml of acetonitrile; 150 g of 4-(4-amino-6-chloropyrimidin-2-ylamino)benzonitrile and 187 g of dimethylaminopyridine were added into a reaction vessel at 27±3° C. and heated to 63±2° C. under stirring. To the reaction mixture was added 425 ml of benzoyl chloride and heated to 78±3° C. and maintained the same for 7 hrs. 50% of acetonitrile was distilled off from the reaction mixture and the reaction mixture cooled to 63±2° C. To the reaction mixture was added 1500 ml of water, stirred for 15 mins at the same temperature and filtered. The obtained product solid was washed with water and suck dried. The wet cake was taken into an RB flask and 1500 ml of methanol was added, stirred and filtered. The obtained solid was washed with 150 ml of methanol and dried under vacuum.

Dry weight: 165-175 gm.

Example 6

Preparation of N-[5-bromo-6-chloro-2-(4-cyanophenylamino)-pyrimidin-4-yl]-benzamide (V)

1000 ml of dichloromethane and 100 g of N-[6-chloro-2-(4-cyanophenylamino)pyrimidin-4-yl]benzamide were added to a reaction vessel. To this was added 76.5 g of N-bromosuccinamide and 2.2 g (10M %) of ammonium acetate and stirred for 4 hrs. After completion of the reaction, the pH was adjusted to 10-11 with 5% of aqueous sodium hydroxide solution (10 g in 200 ml water). The reaction mass was filtered and the wet cake was slurried in 1000 ml of hot water at 55-60° C. for 1 hr and filtered. The obtained solid was dried under vacuum (0.5 kg/cm$^2$) at 55-60° C. overnight.

Practical yield=100 g.

Example 7

Preparation of N-[5-bromo-6-chloro-2-(4-cyanophenylamino)-pyrimidin-4-yl]-benzamide (V)

1500 ml of dichloromethane and 150 g of N-[6-chloro-2-(4-cyanophenylamino)pyrimidin-4-yl]benzamide were added to a reaction vessel and to this was added 750 ml of acetic acid and 44.2 mL of liquid bromine solution at 27±3° C. and stirred for 11 hrs. After completion of the reaction, to the reaction mixture was added 375 ml of water under stirring and maintained for 45 mins. To the reaction mixture was further added metabisulphate solution (60 g in 375 ml of water) and stirred further for 30 mins. The solid was filtered and washed with 300 ml of water and suck dried. The wet cake and 1500 ml of water were charged into a clean RB and adjusted pH 9.0±0.5 with 50% potassium carbonate solution. The reaction mass was stirred and filtered; the solid was washed with 150 ml of water followed by 150 ml of dichloromethane. The obtained solid was dried under vacuum at 73±2° C. to yield the title compound.

Dry weight: 140-165 gm.

Example 8

Preparation of N-[5-bromo-6-(4-cyano-2,6-dimethylphenoxy)-2-(4-cyano-phenylamino)pyrimidin-4-yl]-benzamide (VI)

1000 ml of dimethylformamide, 51.52 g of 3,5-dimethyl-4-hydroxybenzonitrile, 106.9 g of diazabicyclo undecene were added to a reaction vessel and stirred at RT. The reaction mixture was maintained at same temperature for 1 hr and 100 g of N-[5-bromo-6-chloro-2-(4-cyanophenylamino)-pyrimidin-4-yl]benzamide added with continued stirring for 30 mins. The reaction mixture was heated to 100-110° C. and further maintained at same temperature for 24 hr. After completion of the reaction, the reaction mixture was cooled to RT and 2000 ml of water added and stirred at RT for 1 hr. The reaction mixture was filtered. The obtained solid was dried under vacuum (0.5 kg/cm$^2$) at 55-60° C. overnight.

Example 9

Preparation of N-[5-bromo-6-(4-cyano-2,6-dimethylphenoxy)-2-(4-cyano-phenylamino)pyrimidin-4-yl]-benzamide (VI)

1300 ml of dimethylformamide was added to a RB flask, to this was added 54 g of 3,5-dimethyl-4-hydroxybenzonitrile, 51.38 g of dimethyl amino pyridine, 68.30 g of diazabicyclo undecene and 150 g of N-[5-bromo-6-chloro-2-(4-cyanophenylamino)-pyrimidin-4-yl]-benzamide at 27±3° C. The reaction mixture was heated to 73±2° C. and maintained at the same for 5 hrs. The reaction mixture was cooled to 27±3° C. and filtered. The filtrate was taken into an RB flask to which was added 300 ml of IPA and stirred for 30 mins. 3000 ml of water was taken in another RB flask and the reaction mass added. The reaction mass was heated to 47±3° C., stirred, cooled to 42±3° C. and filtered hot. The solid was washed with water and suck dried at 27±3° C. The solid was further washed with 150 ml of IPA and the wet cake was charged into a clean RB flask. To this was added 1500 ml of dimethyl formamide and heated to 47±3° C. To the reaction mass was slowly added 3000 ml of water with continued stirring, followed by cooling the reaction mass to 27±3° C. The reaction mass was filtered, and the solid was washed with water followed by IPA. The solid was then dried under vacuum to yield the title compound.

Dry weight: 130-170 gm.

Example 10

Preparation of Etravirine 400 ml of iso-propyl alcohol and 50 g of N-[5-bromo-6-(4-cyano-2,6-dimethylphenoxy)-2-(4-cyano-phenylamino)-pyrimidin-4-yl]-benzamide were added to a reaction vessel and stirred at RT. Separately, prepared sodium hydroxide solution, i.e. sodium hydroxide (12.5 g) in water (100 ml) was added to the reaction mixture and stirred at RT for 30 mins. and heated to 70-75° C. The reaction mixture was maintained at the same temperature for 5 hrs. After completion of the reaction, reaction mixture was cooled to RT, filtered. The solid obtained was dried under vacuum at 55-60° C. overnight.

Purification:

600 ml of acetone was added to a reaction vessel, to this was added the above obtained solid (1 eq) and heated to reflux and the same was maintained for 1 hr. The reaction mixture was then cooled to RT, and acetone distilled out under reduced pressure until 250 ml of acetone remained. The reaction mixture was cooled to RT and filtered. The solid obtained was dried under vacuum (0.5 kg/cm$^2$) at 55-60° C. for 5 hr.

Practical yield=24 g.

Example 11

Preparation of Etravirine 1350 ml of acetonitrile was taken into a RB flask at 27±3° C. To this was added 900 ml of IPA. To the reaction mixture 150 g of N-[5-bromo-6-(4-cyano-2,6-dimethylphenoxy)-2-(4-cyano-phenylamino)pyrimidin-4-yl]benzamide and 35.2 g of lithium hydroxide monohydrate were added and heated to 59±3° C. The reaction mixture was maintained at the same temperature for 10 hrs. After completion of the reaction, the reaction mixture was cooled to 47±3° C. and filtered. The solid was washed with acetonitrile and suck dried. The wet cake was taken into another flask to which was added 1500 ml of water, stirred for 30 mins and filtered to obtain the solid. The solid was washed with water and dried under vacuum at 73±3° C. to isolate Etravirine.

Dry weight: 70-75 g.

Purification of Etravirine:

1000 ml of acetone and 100 g of crude Etravirine were added to an RB flask at 27±3° C. and heated to 53±3° C. The reaction was maintained at the same temperature to form a clear solution. The hot solution was filtered through celite and washed with 200 ml of hot acetone. The acetone was distilled off under vacuum until 200 ml remained in the reaction mixture and cooled to 27±3° C. 1500 ml of water was added to the reaction mixture, stirred and filtered. The solid was washed with water and dried under vacuum.

Dry weight: 90-93 g.

The invention claimed is:

1. A process for preparing Etravirine comprising the steps of:

a) converting the OH group of a compound of formula (II)

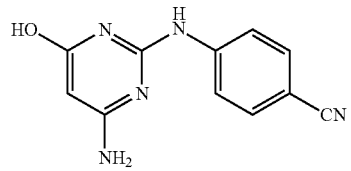

(II)

into a leaving group of a compound of formula (III)

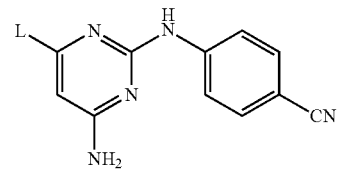

(III)

b) optionally protecting the compound of formula (III) to a compound of formula (IV),

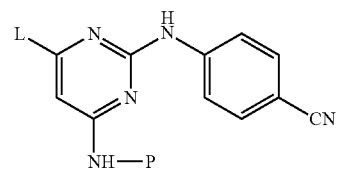

(IV)

c) brominating the compound of formula (IV) to obtain a compound of formula (V)

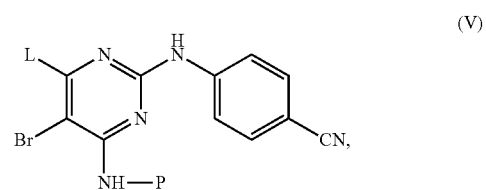

(V)

wherein L is leaving group and P is hydrogen or a suitable amino protecting group, d) condensing the compound of formula (V) with 3,5-dimethyl-4-hydroxybenzonitrile to obtain a compound of formula (VI), and

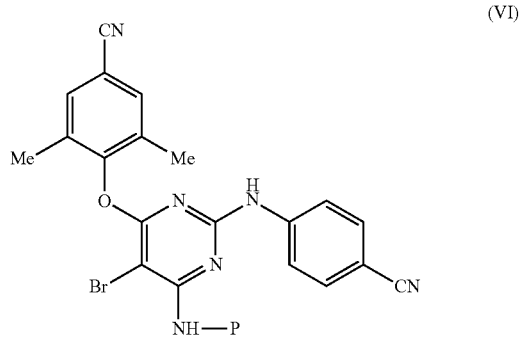

(VI)

e) if necessary, deprotecting the compound of formula (VI).

2. The process according to claim 1, wherein the leaving group of the compound formula (III) is chloro.

3. The process according to claim 2, wherein the compound of formula (III) is prepared by treating the compound of formula (II) with a chlorinating agent selected from the group consisting of chlorine, phosphorus oxychloride, phosphorus pentachloride, phosphorus trichloride and thionyl chloride.

4. The process according to claim 1, wherein the amino protecting group is selected from the group consisting of carbobenzyloxy (Cbz), p-methoxybenzyl carbonyl, tert-butyloxycarbonyl (BOC), 9-fluorenylmethyloxycarbonyl (FMOC), acetyl (Ac), benzoyl (Bz), benzyl (Bn), carbamate group, p-methoxybenzyl (PMB), 3,4-dimethoxybenzyl (DMPM), p-methoxyphenyl (PMP), tosyl (Ts) and sulfonamides.

5. The process according to claim 4, wherein the protection of the compound of formula (III) is carried out by treating the compound of formula (III) with benzoyl chloride in the presence of a base in suitable organic solvent.

6. The process according to claim 1, wherein the bromination of the compound of formula (IV) is carried out by a treatment with bromine in the presence of an acid.

7. The process according to claim 1, wherein the compound of formula (II) is prepared by condensing ethyl cyanoacetate with N-cyanophenyl guanidine.

8. The process according to claim 7, wherein the condensation is carried out in the presence of a base in a solvent.

9. The process according to claim 8, wherein the base is potassium-tert-butoxide and the solvent is n-butanol.

10. A process for preparing Etravirine comprising the steps of:

a) condensing ethyl cyanoacetate with N-cyanophenylguanidine to get a compound of formula (II),

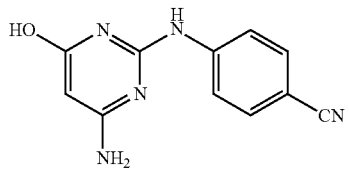

(II)

b) converting the —OH group of the compound of formula (II), into a leaving group of a compound of formula (III),

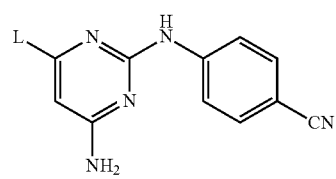

(III)

L is a leaving group c) optionally protecting the amino group of the compound of formula (III) to get a compound of formula (IV),

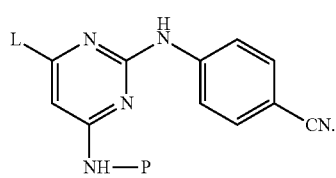

(IV)

L is a leaving group,
P is Hydrogen or protecting group d) brominating the compound of formula (IV) to get a compound of formula (V),

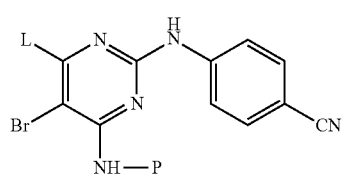

(V)

e) condensing the compound of formula (V) with 3,5-dimethyl-4-hydroxybenzonitrile to get a compound of formula (VI), and

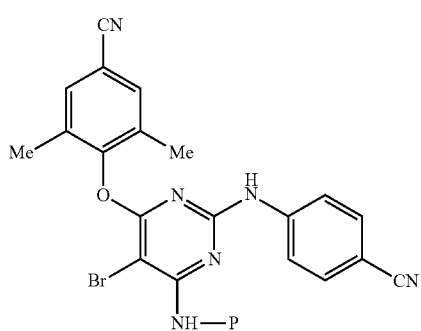

(VI)

optionally deprotecting the compound of formula (VI) to get Etravirine.

11. A process for the preparation of Etravirine comprising the use of at least one of:

a compound of formula (II)

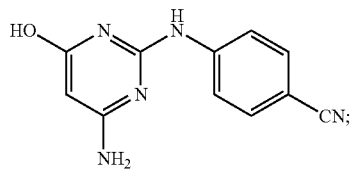

(II)

a compound of formula (III)

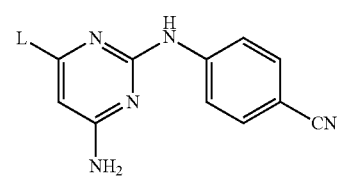

(III)

wherein L is a leaving group;
a compound of formula (IV)

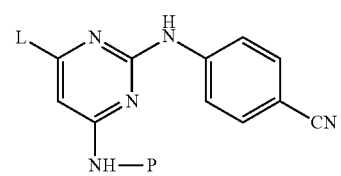

(IV)

wherein L is a leaving group and P is a suitable amine protecting group;
a compound of formula (V)

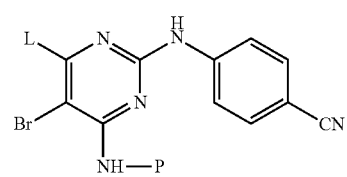

(V)

wherein L is a leaving group and P is a suitable amine protecting group; or
a compound of formula (VI)

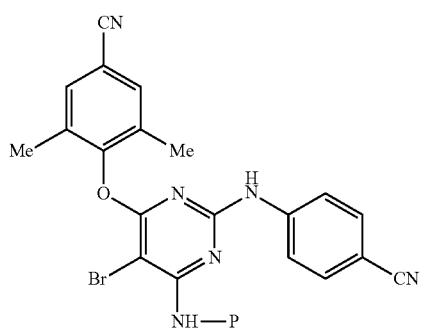

(VI)

wherein L is a leaving group and P is a suitable amine protecting group.

* * * * *